(12) United States Patent
Courvoisier

(10) Patent No.: US 9,770,247 B2
(45) Date of Patent: Sep. 26, 2017

(54) METHOD FOR MANUFACTURING DISPOSABLE ROTARY CUTTING TOOLS AND DISPOSABLE ROTARY TOOL FOR DENTAL OR MEDICAL APPLICATIONS

(75) Inventor: Stephane Courvoisier, Colombier (CH)

(73) Assignee: Straumann Holding AG, Basel (CH)

( * ) Notice: Subject to any disclaimer, the term of this patent is extended or adjusted under 35 U.S.C. 154(b) by 1165 days.

(21) Appl. No.: 12/418,728

(22) Filed: Apr. 6, 2009

(65) Prior Publication Data
US 2009/0208903 A1    Aug. 20, 2009

Related U.S. Application Data

(63) Continuation of application No. 11/156,159, filed on Jun. 17, 2005, now Pat. No. 7,559,765.

(30) Foreign Application Priority Data

Jun. 21, 2004 (EP) .................................... 04014491

(51) Int. Cl.
*A61C 3/02* (2006.01)
*A61B 17/16* (2006.01)
(Continued)

(52) U.S. Cl.
CPC .......... *A61B 17/16* (2013.01); *A61B 17/1615* (2013.01); *A61B 17/1637* (2013.01);
(Continued)

(58) Field of Classification Search
CPC ..... A61B 17/16; A61B 90/94; A61B 17/1615; A61B 17/1637; A61B 2090/062; A61B 2090/0814; A61B 17/1617; A61B 17/162; A61B 17/1635; A61C 3/02; A61C 8/0089; B23B 49/00; B23B 49/005; B23B 51/00; B23B 51/04; B23B 51/0406; B23B 51/0473; B23B 2251/02; B23B 210/02; B23B 2210/03; B23C 5/10; B23P 15/32; Y10T 408/906; Y10T 408/907; Y10T 407/1938; Y10T 29/49945; Y10T 29/4998
(Continued)

(56) References Cited

U.S. PATENT DOCUMENTS 2,695,452 A    11/1954  Christian
2,886,081 A     5/1959  Cowley
(Continued)

FOREIGN PATENT DOCUMENTS

FR    2554709 A     5/1985
GB     742281 A    12/1955
GB    1147786 A     4/1969

OTHER PUBLICATIONS

European Search Report dated Dec. 3, 2004 in corresponding European Patent Application No. 04014491.7.
(Continued)

*Primary Examiner* — Heidi M Eide
(74) *Attorney, Agent, or Firm* — Polsinelli PC

(57) ABSTRACT

The shank (12) of a disposable rotary cutting tool (10) comprises a pipe section (16) cut from a drawn metal pipe. The tool head (14) is formed from a cut-out (18a, 18b) of a drawn metal sheet or a section of a metal tube by non-cutting machining. The pipe section (16) and the tool head (14) are advantageously attached by force fitting.

4 Claims, 11 Drawing Sheets

(51) Int. Cl.

| | |
|---|---|
| *A61C 8/00* | (2006.01) |
| *B23B 49/00* | (2006.01) |
| *B23B 51/00* | (2006.01) |
| *B23B 51/04* | (2006.01) |
| *B23C 5/10* | (2006.01) |
| *B23P 15/32* | (2006.01) |
| *B23P 15/28* | (2006.01) |
| *A61B 90/94* | (2016.01) |
| *A61B 90/00* | (2016.01) |

(52) U.S. Cl.
CPC ............... *A61B 90/94* (2016.02); *A61C 3/02* (2013.01); *A61C 8/0089* (2013.01); *B23B 49/00* (2013.01); *B23B 49/005* (2013.01); *B23B 51/00* (2013.01); *B23B 51/04* (2013.01); *B23B 51/0406* (2013.01); *B23B 51/0473* (2013.01); *B23C 5/10* (2013.01); *B23P 15/28* (2013.01); *B23P 15/32* (2013.01); *A61B 17/162* (2013.01); *A61B 17/1617* (2013.01); *A61B 17/1635* (2013.01); *A61B 2090/062* (2016.02); *A61B 2090/0814* (2016.02); *B23B 2251/02* (2013.01); *B23C 2210/02* (2013.01); *B23C 2210/03* (2013.01); *Y10T 29/4998* (2015.01); *Y10T 29/49567* (2015.01); *Y10T 29/49945* (2015.01); *Y10T 407/1938* (2015.01); *Y10T 408/906* (2015.01); *Y10T 408/909* (2015.01)

(58) Field of Classification Search
USPC ............... 433/165, 166; 408/224, 226, 227; 606/180
See application file for complete search history.

(56) References Cited

U.S. PATENT DOCUMENTS

| | | | |
|---|---|---|---|
| 3,865,502 A | | 2/1975 | Hamann |
| 4,178,688 A | * | 12/1979 | Polanin .................. 433/220 |
| 4,283,175 A | * | 8/1981 | Nash ...................... 433/119 |
| 4,478,578 A | | 10/1984 | Leonard |
| 4,664,567 A | | 5/1987 | Edwards |
| 4,787,848 A | * | 11/1988 | Ross ...................... 433/165 |
| 4,820,156 A | * | 4/1989 | Ross ...................... 433/165 |
| 4,944,677 A | | 7/1990 | Alexandre |
| 5,085,586 A | | 2/1992 | Johnson |
| 5,211,560 A | | 5/1993 | Lowder et al. |
| 5,261,818 A | | 11/1993 | Shaw |
| 5,306,301 A | | 4/1994 | Graf et al. |
| 5,429,199 A | | 7/1995 | Sheirer et al. |
| 5,505,617 A | | 4/1996 | Skeppmark et al. |
| 5,556,399 A | * | 9/1996 | Huebner .................. 606/80 |
| 5,868,572 A | * | 2/1999 | Lazzara et al. ........... 433/173 |
| 5,897,318 A | | 4/1999 | Badoz |
| 5,941,706 A | * | 8/1999 | Ura ........................ 433/165 |
| 6,062,859 A | | 5/2000 | Filhol |
| 6,106,292 A | | 8/2000 | Hollander et al. |
| 6,168,599 B1 | | 1/2001 | Frieze et al. |
| 6,514,258 B1 | * | 2/2003 | Brown et al. ............ 606/80 |
| 6,742,236 B1 | | 6/2004 | Mayville et al. |
| 2001/0013266 A1 | * | 8/2001 | Isaksson ................. 81/180.1 |
| 2003/0022132 A1 | * | 1/2003 | Jesch ..................... 433/165 |
| 2003/0185640 A1 | | 10/2003 | Ito |

OTHER PUBLICATIONS

Sep. 22, 2010 U.S. Office Action in parent U.S. Appl. No. 12/418,691.

* cited by examiner

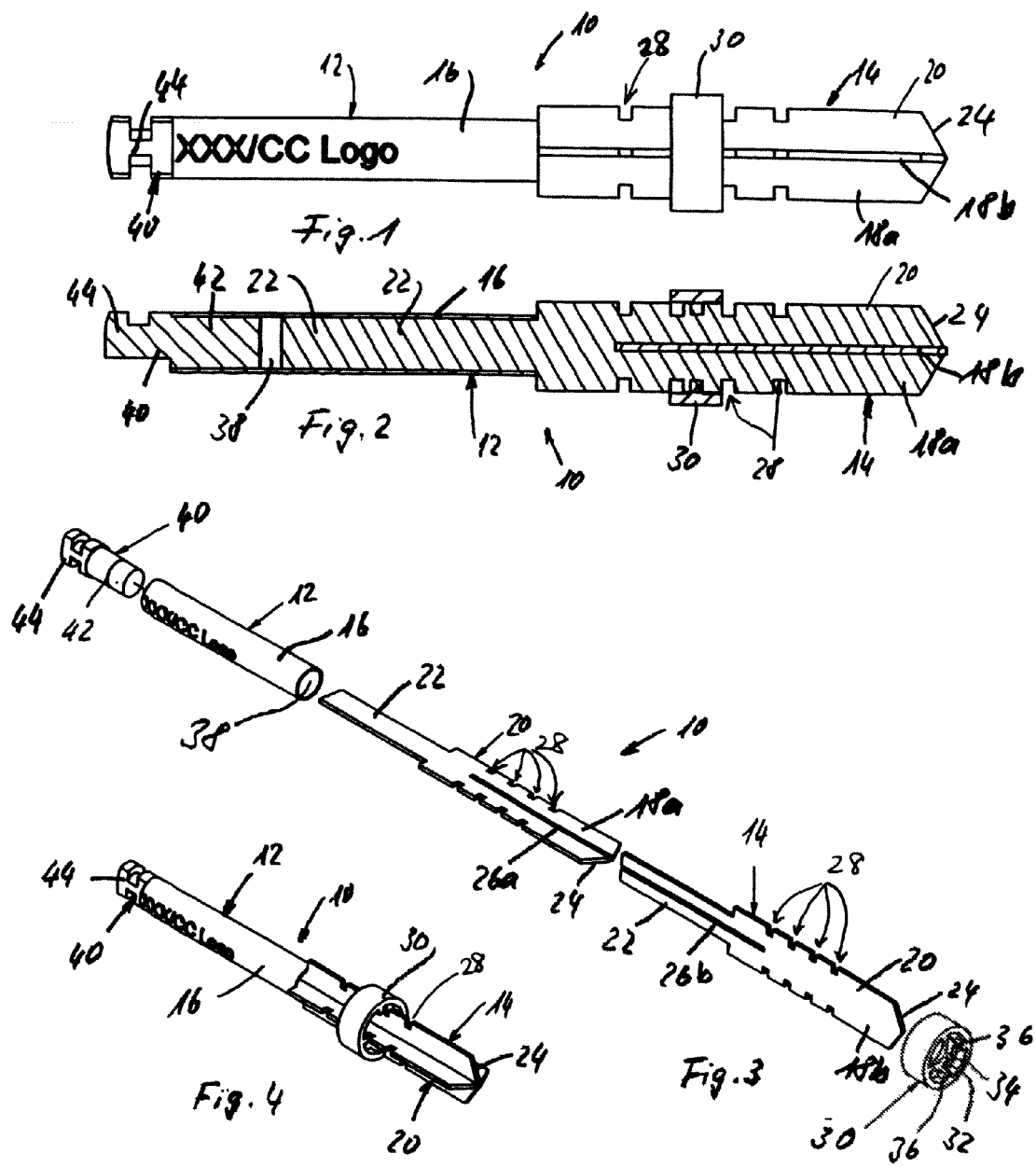

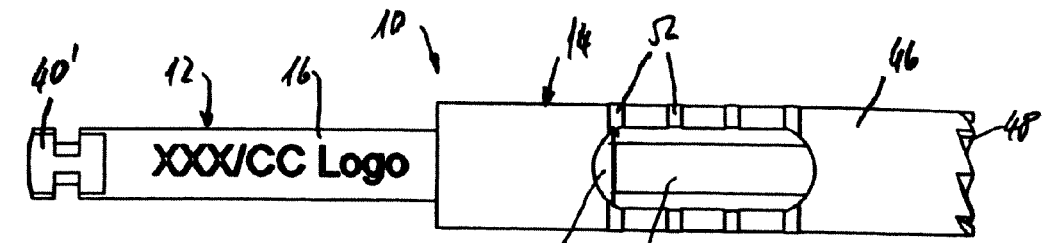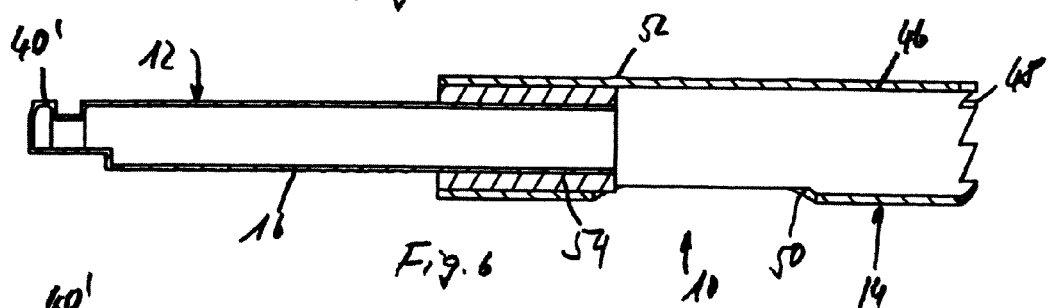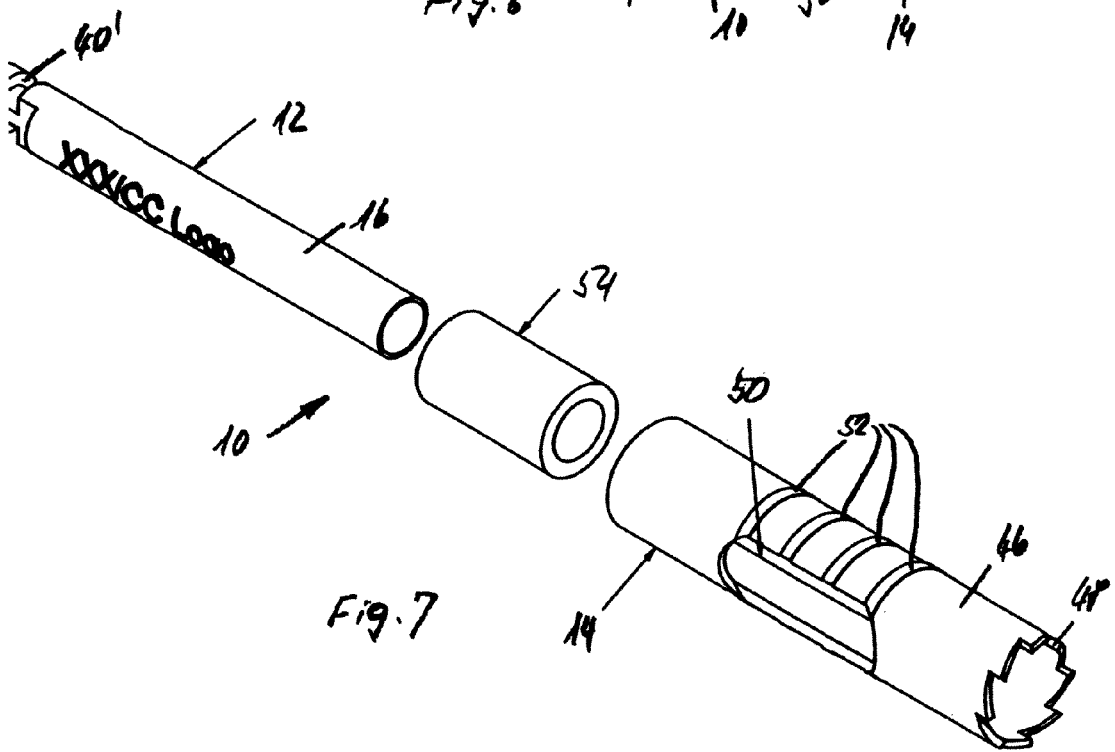

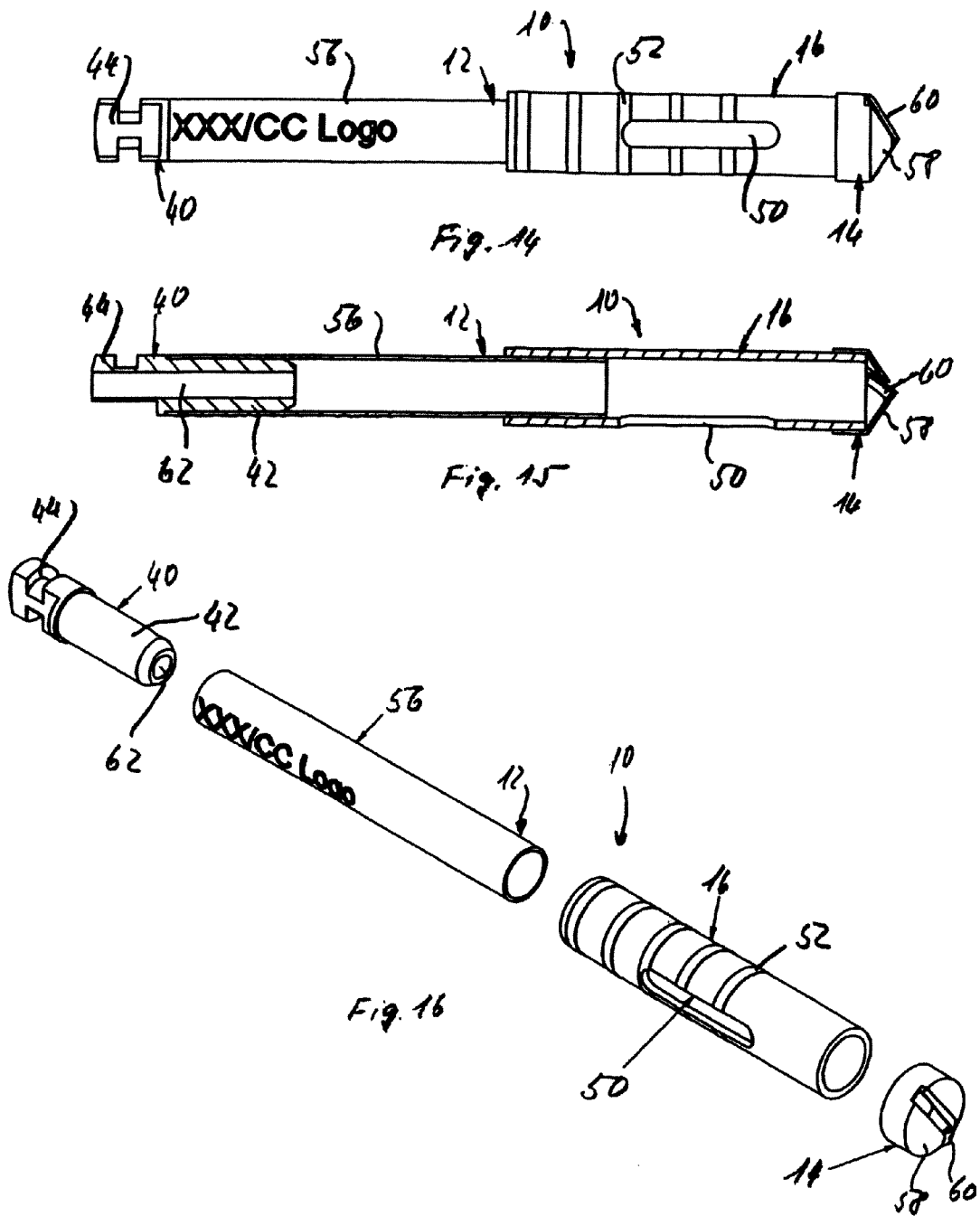

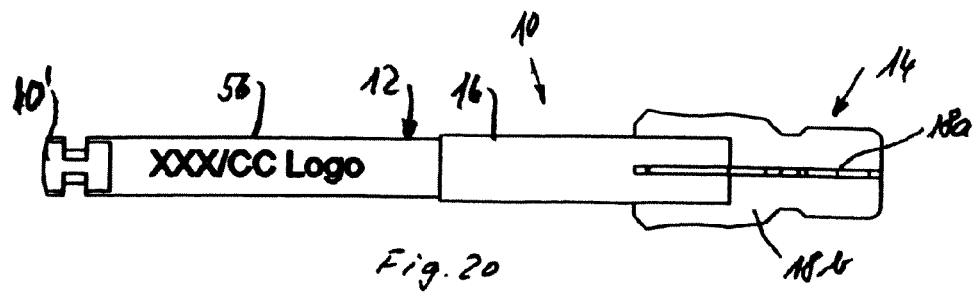
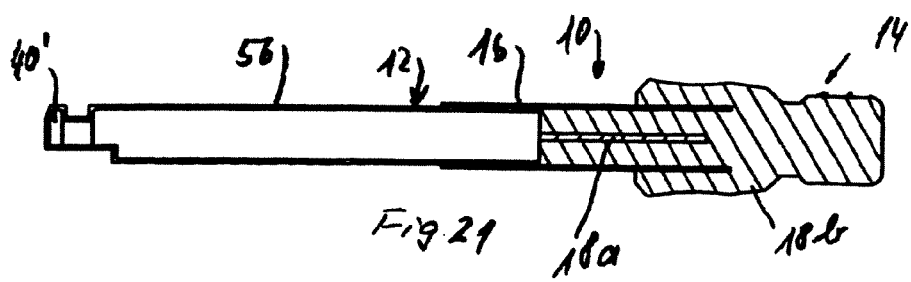
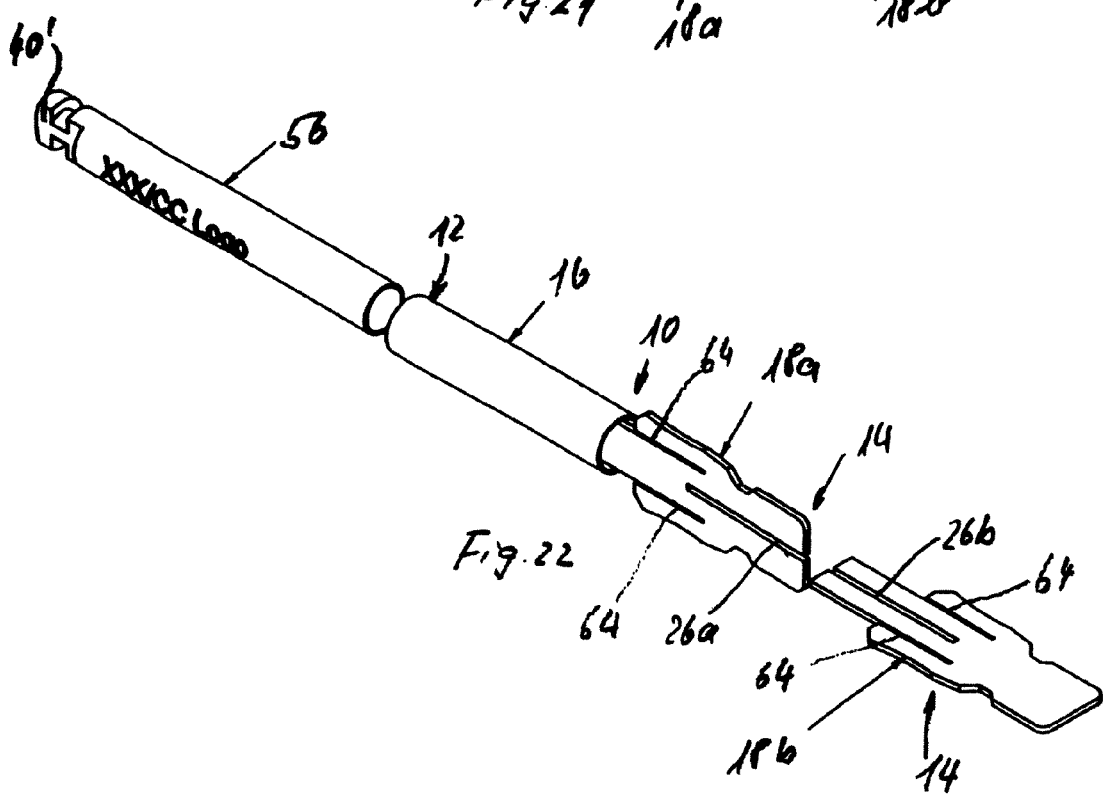

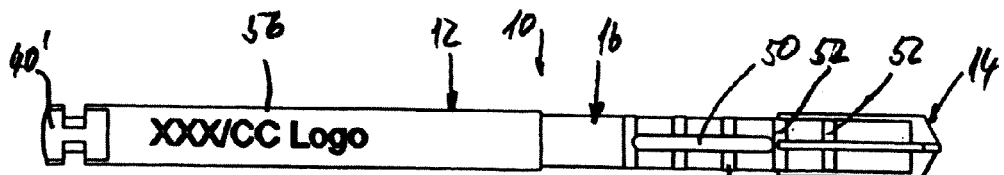
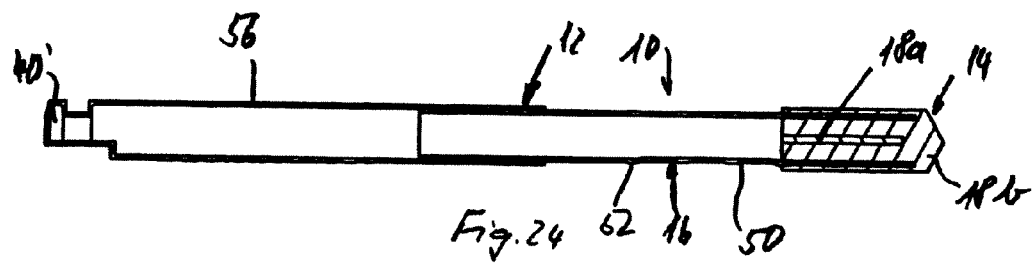
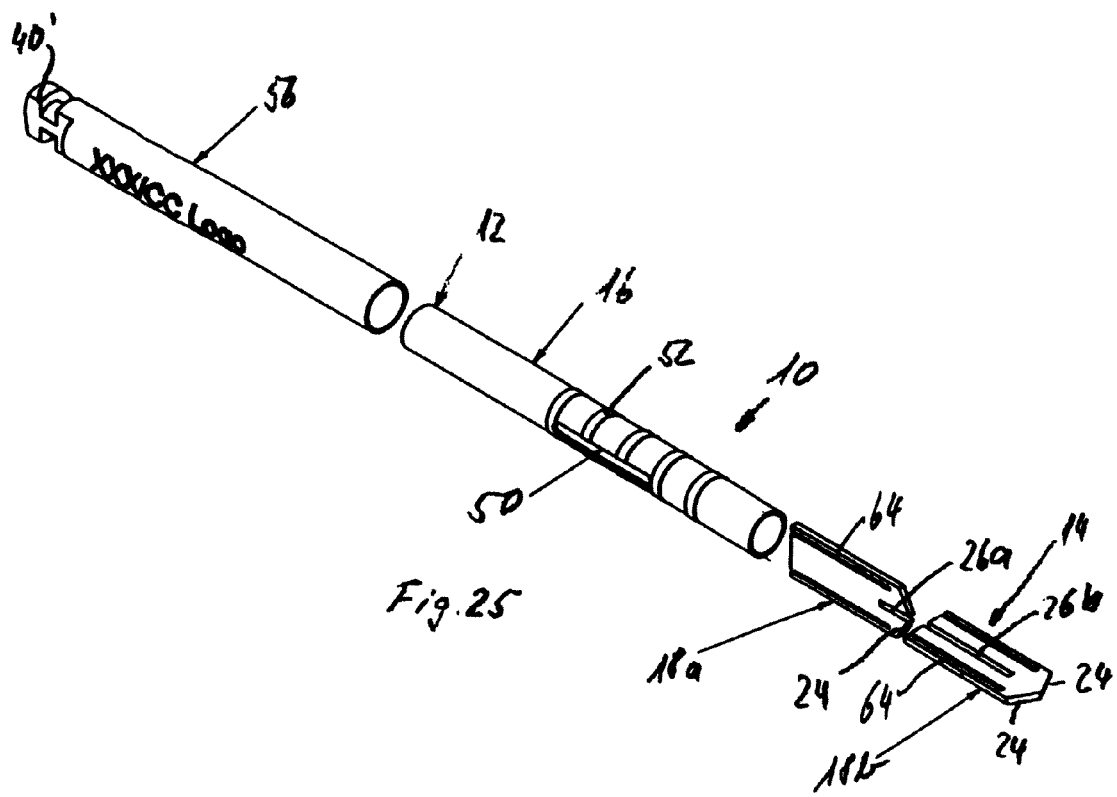

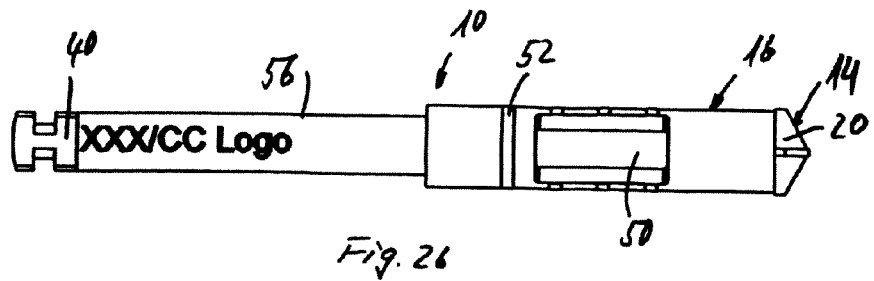
Fig. 26
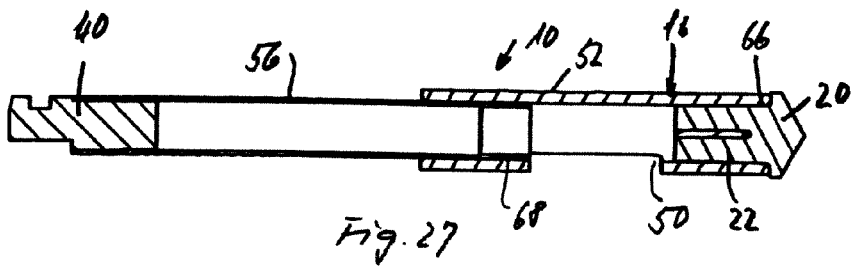
Fig. 27
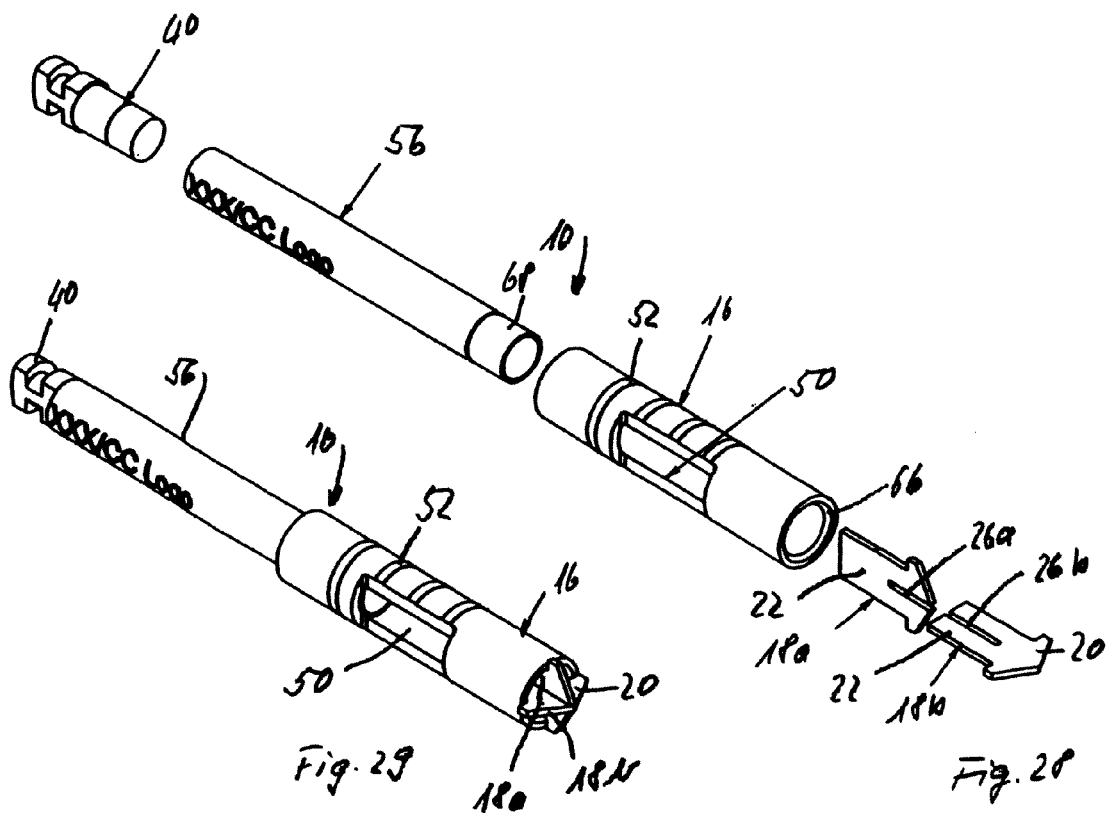
Fig. 28
Fig. 29

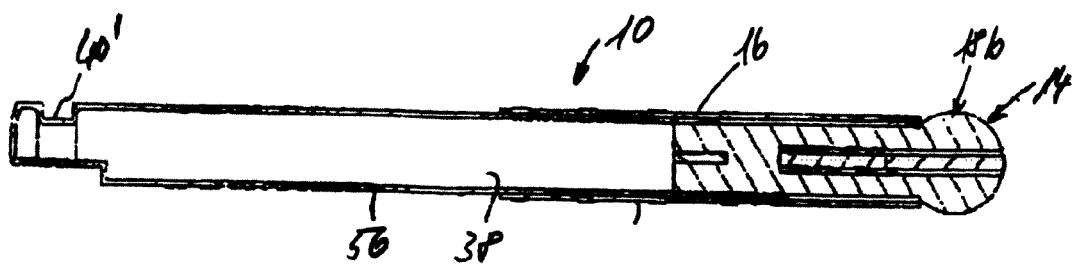
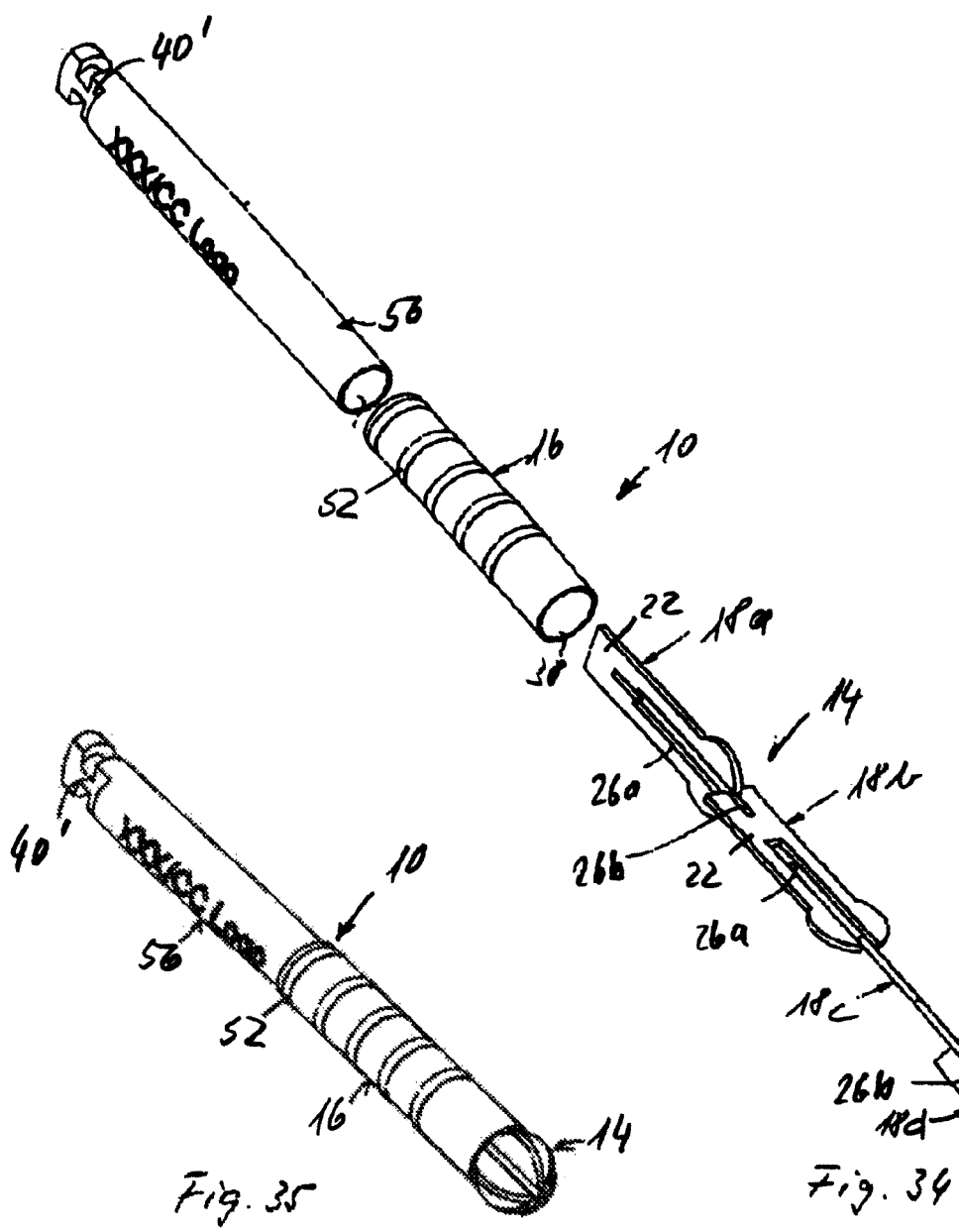

METHOD FOR MANUFACTURING DISPOSABLE ROTARY CUTTING TOOLS AND DISPOSABLE ROTARY TOOL FOR DENTAL OR MEDICAL APPLICATIONS

FIELD OF THE INVENTION

The present invention relates to a method for manufacturing disposable rotary cutting tools for dental or medical applications and a disposable rotary cutting tool for dental or medical applications.

BACKGROUND

There are a large number of cutting tools on the market for various applications in the medical or dental field, in particular for applications involving drilling, tapping, milling, smoothing, forming and other cutting functions in a bone or a tissue. For example, in the dental field, drills are used for drilling holes in the jawbone. A tap is then used, and perhaps also a profiling tool, so that an anchoring support can be screwed in order to fix a tooth crown. In the medical field, profiling, smoothing and milling tools are used in order to drill, profile or smooth the bony material or to remove deposits.

Most of the cutting tools available on the market are tools made from steel of medical quality, which are manufactured at least partially by machining with removal of chips. These tools generally being made for multiple use, inter alia on account of their relatively high manufacturing costs. There is, however, an increasing demand and for disposable tools, i.e. for once-only use, on account of the risks of the transmission of diseases, but also because of the costs of the sterilization of reusable tools.

RU-C-2 167 618 discloses a disposable needle-type drill for bone tissue. The drill comprises a casing made in the form of a tube or continuos rod with a flat or square portion. A front working part of the drill is provided with cutting members formed as longitudinally arranged needles. This known drill may be used for performing operations in traumatology, neuro-surgery etc.

Drills for the insertion of dental implants, that can be disposed of after each use, are disclosed in U.S. Pat. No. 5,839,897. The drill includes a rotational drive portion in the form of a metal rod with a first end and a second end. The first end is intended to be connected to a drilling apparatus. The second end is connected to an active cutting portion made of plastic overmolded on the second end of the metal rod. The drill further includes a metal insert portion coupled to the active cutting portion to serve as a sharp edge for the active cutting portion.

The disposable rotary cutting tools disclosed in these prior art documents comprise parts being injection-molded or complexly machined and not making it possible to carry out simple modifications of the tool for different applications. Further more, plastic parts for such tools are usually not readily accepted in invasive applications because of the risks of breakage of the plastic and of the deposit of plastic particles during the surgical operation.

SUMMARY OF THE INVENTION

According to one or more embodiments of the present invention, a method is provided for manufacturing disposable rotary cutting tools for dental or medical applications in large series at low cost. According to other embodiments, low cost disposable rotary cutting tools are provided for dental and medical applications that are reliable and safe.

The term "cutting tool" is used to refer, in general, to all rotating tools making it possible to work the bone or tissue by cutting or by abrasion for various functions, such as drilling, milling, smoothing and profiling of, more particularly, a bone, but also a tissue.

According to one embodiment, at least a part of a shank of the tool is formed from a pipe section cut from a metal pipe. A tool head is formed from a metal sheet or tube. The tool shank and the tool head are manufactured separately and assembled together.

Advantageously, the modular construction of the tool for once-only use according to this embodiment allows a high degree of versatility in the manufacture of different tools, in that, for example, simply the tool head and/or the tool shank is/are changed. Producing at least a part of the tool shank in the form of a pipe section is highly advantageous in terms of the manufacturing costs in large series. On the other hand, it makes it possible to assemble the tool head and the tool shank by means of simple operations, such as driving in, while at the same time ensuring good mechanical resistance and the absence of the use of plastic in the invasive part of the tool.

A further working of the pipe section, for example by drawing, swaging or stamping, is advantageous in a high volume fabrication.

To detach a cut-out from a metal sheet or a tube section from a metal tube by non-cutting machinery and the forming of the tool head by non-cutting machinery, in particular by punching, swaging or stamping, is inexpensive and generates at the same time the sharp edges for treating the bone or tissue.

Drawn metal pipes, metal sheets and metal tubes are especially well suited for manufacturing the tool shank and the tool head.

Driving the pipe section of the tool shank and the tool head into one another in order to assemble them and especially a force fitting is advantageous from the point of view of the manufacturing costs, while at the same time ensuring high mechanical resistance and therefore safety against the risk of breakage of the tool.

In a further preferred embodiment, the pipe section may be equipped with a small cut-out monitoring window, thus making it possible to take a sample of the drilled bone or tissue or to ascertain whether the tool has already been used or not.

For some applications, the tool head my be formed from more than one cut-out forming blade. Where a plurality of cut-outs are concerned, the cut-outs are advantageously equipped with complementary slots in order to be inserted one into the other and driven into the pipe section.

Further advantageous characteristics may be gathered from the following description and from the accompanying drawings.

BRIEF DESCRIPTION OF THE DRAWINGS

FIG. 1 is a plane view of a first cutting tool according to an embodiment of the invention, this tool being used for drilling holes to a depth determined by a stop provided for this purpose;

FIG. 2 is a longitudinal sectional view of the first cutting tool;

FIG. 3 is an exploded perspective view of the first cutting tool;

FIG. 4. is a perspective view of the first cutting tool;

FIG. 5 is a plane view of a second cutting tool according to another embodiment, this tool being used for drilling annular ducts and for taking samples of tissue or bone;

FIG. 6 is a longitudinal sectional view of the second cutting tool;

FIG. 7 is an exploded perspective view of the second cutting tool;

FIG. 14 is a plane view of a fifth cutting tool according to another embodiment, similar to the third and fourth cutting tools;

FIG. 15 is a longitudinal sectional view of the fifth cutting tool;

FIG. 16 is an exploded perspective view of the fifth cutting tool;

FIG. 20 is a plane view of a seventh cutting tool according to another embodiment, being used as a profiling tool;

FIG. 21 is a longitudinal sectional view of the seventh cutting tool;

FIG. 22 is an exploded perspective view of the seventh cutting tool;

FIG. 23 is a plane view of an eighth cutting tool according to another embodiment, being used for drilling operations;

FIG. 24 is a longitudinal sectional view of the eighth cutting tool;

FIG. 25 is an exploded perspective view of the eighth cutting tool;

FIG. 26 is a plane view of a ninth cutting tool according to another embodiment, being used as a drilling or chamfering tool or as a tool for forming conical cups in the bone;

FIG. 27 is a longitudinal sectional view of the ninth cutting tool;

FIG. 28 is an exploded perspective view of the ninth cutting tool;

FIG. 29 is a perspective view of the ninth cutting tool;

FIG. 33 is a longitudinal sectional view of an eleventh cutting tool according to another embodiment, this tool being used for forming spherical cups in the bone;

FIG. 34 is an exploded perspective view of the eleventh cutting tool; and

FIG. 35 is a perspective view of the eleventh cutting tool.

DETAILED DESCRIPTION

Figure 8:
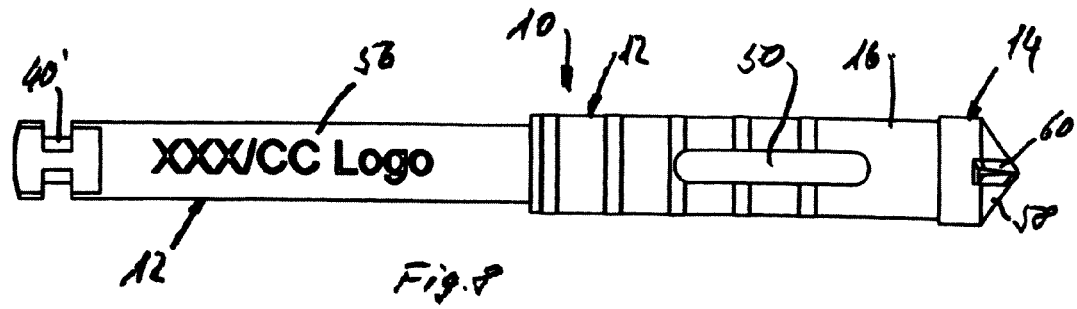
FIG. 8 is a plane view of a third cutting tool according to another embodiment, this tool being used for drilling operations.

The first embodiment of a cutting tool 10 shown in FIGS. 1 to 4 comprises a tool shank 12 and a tool head 14. The tool shank 12 consists of a pipe section 16 cut from a drawn metal pipe. The shell of the pipe section 16 is parameterized and branded.

The tool head 14 is formed by two cut-outs 18 of a drawn metal sheet, that are arranged in a crosswise manner. The cut-outs 18a, 18b are detached form the metal sheet by non-cutting machining, for example by punching. The thereby produced sharp edges are not further machined.

The cut-outs 18a, 18b have an essentially rectangular formed working portion 20 and an adjacent integral rectangular fastening portion 22. A front edge 24 of the working portion 20 is indeed formed to a vertex whereby the front edge portions enclose an obtuse angle.

Furthermore, the cut-outs 18a, 18b comprise complementary slots 26a, 26b, i.e. the cut-out 18a has a slot 26a running along a central axis of the cut-out 18a from the front end of the cut-out 18a to the middle of the cut-out 18a, and the cut-out 18b has a corresponding slot 26b running from the rear end to the middle. By these slots 26a and 26b, the two cut-outs 18a and 18b can be retracted one into the other to build the tool head 14 with two crosswise arranged blades.

The lateral edges of the working portion 20 of the cut-outs 18a, 18b running in the longitudinal direction comprise four rectangular recesses 28. These recesses 28 serve for the immobilization of a stop 30 in the form of an injection-molded plastic ring at a desired position. For that purpose, the stop 30 comprises on the inside a bead 32 running in a circumferential direction and having four interrupts 34. If the interrupts 34 align with the assembled cut-outs 18a, 18b, the stop 30 can be moved in the longitudinal direction of the tool head to the desired recesses 28. By rotating the stop 30, the bead 32 comes in engagement with the desired recesses 28 and axial movement of the stop 30 is prevented.

In the middle between each of two interrupts 34, the stop 30 comprises protrusions 36 constituting limit stops limiting the rotational movement of the stop 30 relative to the tool head 14.

The width of each fastening portion 22 of the cut-outs 18a, 18b is determined such that the fastening portions 22 of the assembled cut-outs 18a, 18b can be driven into the central duct 38 to a force fitting.

Finally, the first cutting tool 10 comprises a fastening connector body 40 with a cylindrical or conical pin portion 42 that is pressed into a rear end region of the central duct 38 of the pipe section 16 to create a firm connection between the fastening connector body 40 and the pipe section 36. The fastening connector body 40 further comprises a connector portion 44—projecting from the pipe section 16—in the form of a standardized connector for fastening the cutting tool 10 in a drive device. The fastening connector body 40 is advantageously produced by injection-molding of plastic. However, the fastening connector body 40 can be made of other materials such as metal.

A second rotary cutting tool 10, shown in the FIGS. 5 to 7, comprises a tubular tool head 14. It is manufactured from a section 46 of drawn metal tube by creating at the front end a crown of saw teeth 48 by non-cutting machining, for example by punching. Moreover, the tube section 46 is cut out or stamped to produce a radial monitoring window 50 making it possible to check whether the cutting tool 10 has been used or not, or to make it possible to take a tissue sample.

The tube section 46 is furthermore stamped, for example by means of profiled rollers, to form annular protuberances 52 serving as reference marks for visualizing the cutting depth.

A bushing 54, for example a section of a further metal tube or of a plastic tube, is inserted into a rear end portion of the tube section 46. A pipe section 16 constituting the tool shank 12, is similarly inserted into the bushing 54. By this, a force-fit connection between the tool head 14, i.e. the tube section 46, and the shank 12, i.e. the pipe section 16, is obtained.

A fastening connector part 40' is integrally formed with the pipe section for example by die squeezing and/or stamping the pipe section 16.

Figure 9:
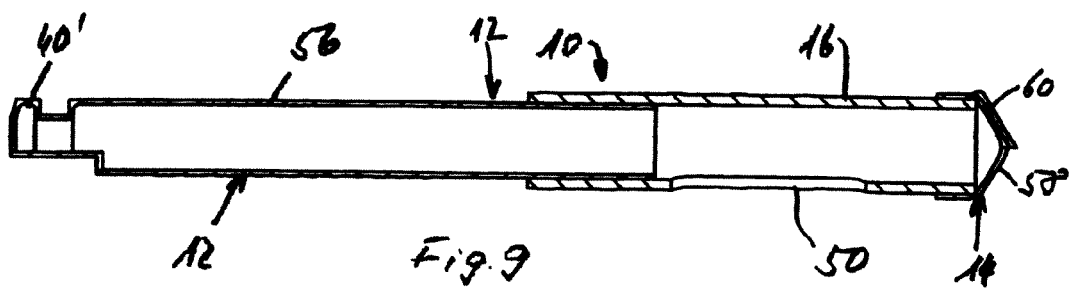
FIG. 9 is a longitudinal sectional view of the third cutting tool.
Figure 10:
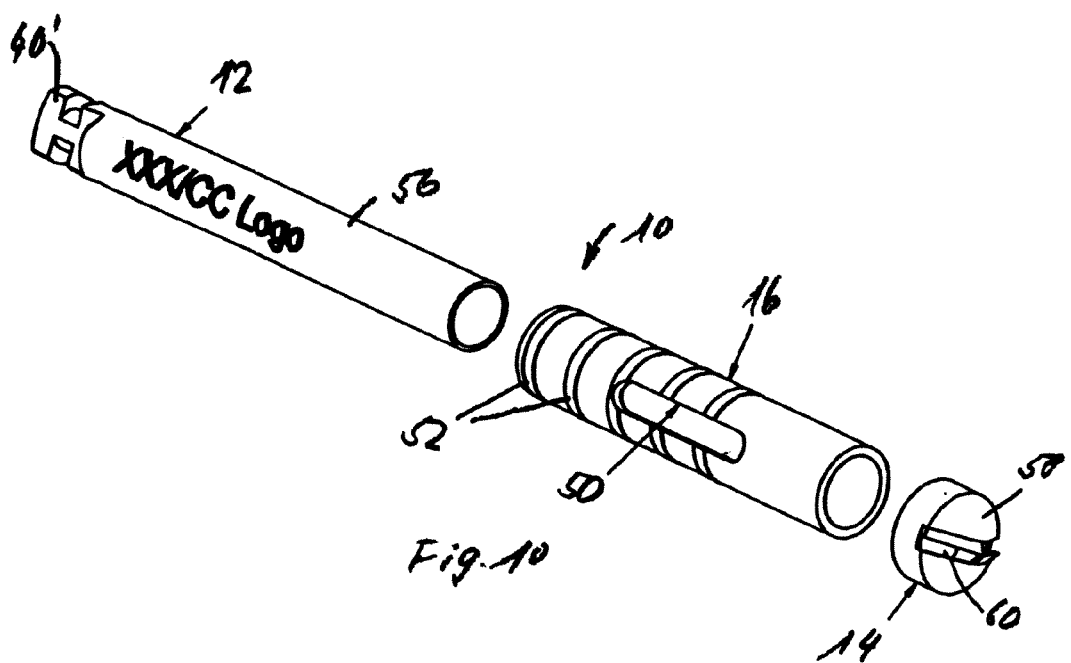
FIG. 10 is an exploded perspective view of the third cutting tool.

The FIGS. 8 to 10 show a third cutting tool 10 comprising a tool shank 12 made of two force-fittingly axially joined pipe sections, a pipe section 16 connected to the tool head 14 and a further pipe section 56.

A comparison of these FIGS. 8 to 10 and the FIGS. 5 to 7 clearly shows that the further pipe section 56 in FIGS. 8 to 10 is precisely identically formed as the pipe section 16 of the embodiment of FIGS. 5 to 7.

The pipe section 16 as shown in FIGS. 8 to 10 is manufactured from a section of a drawn metal pipe, whose bore is slightly smaller than the outer diameter of the further pipe section 56.

As the tube section 46 of the tool head 14 of the embodiment shown in FIGS. 5 to 7, the pipe section 16 of the embodiment according to FIGS. 8 to 10 comprises a monitoring window 50 and protuberances 52.

The tool head 14 shown in FIGS. 8 to 10 is a swaged and/or stamped cut-out 18 of a drawn metal sheet. The bottom 58 of the cup-like tool head 14 is cone-shaped and comprises a cutting blade 60 built by a bar-like part of the bottom 58 bent out of the conical shape. The cutting edge is formed by the burr of the cutting blade 60.

The tool head 14 is hat-like attached on the front end region of the pipe section 16 in a force fitting manner.

Figure 11:
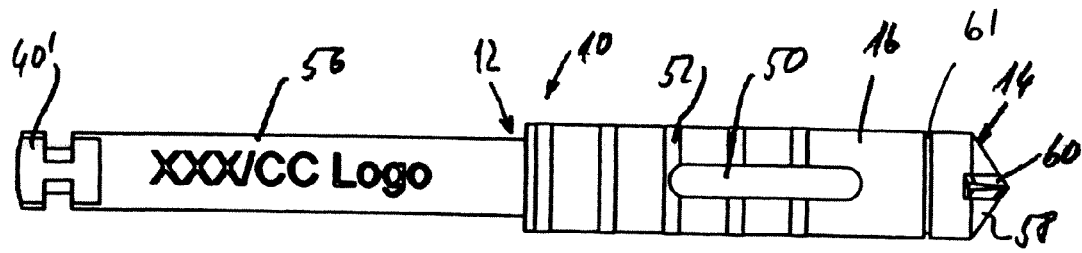
FIG. 11 is a plane view of a forth cutting tool according to another embodiment, similar to the third cutting tool.
Figure 12:
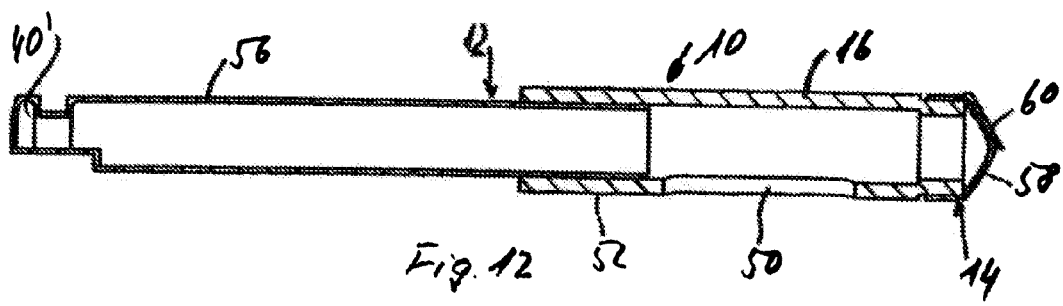
FIG. 12 is a longitudinal sectional view of the fourth cutting tool.
Figure 13:
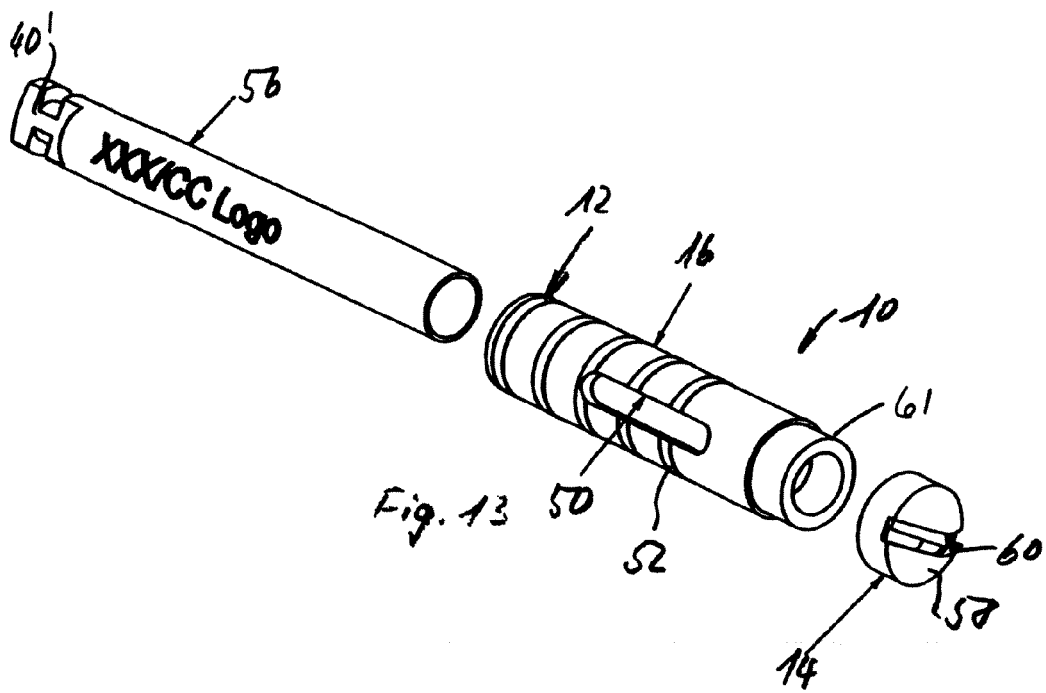
FIG. 13 is an exploded perspective view of the fourth cutting tool.

The design of a fourth cutting tool 10 shown in FIGS. 11 to 13 is just the same as of the cutting tool 10 accordingly to FIGS. 8 to 10 with the exception that the pipe section 16 comprises in its front end region a circumferential contraction 61 formed for example by stamping, swaging or rolling. The diameter of the tool head 14 is accordingly smaller so that the outer shell of the tool head 14, when attached to the pipe section 16, is flush with the outer surface of the pipe section 16.

The tool head 14 and pipe section 16 of a fifth cutting tool 10 shown in FIGS. 14 to 16 has accurately the same design as the embodiment shown in FIGS. 8 to 10 and described above. The further pipe section 56, force-fittingly attached to the pipe section 16, has the same design as the pipe section 16 shown in and described in connection with FIGS. 1 to 4. A fastening connector body 40 is plugged with its pin portion 42 in the rear end region of the further pipe section 56. The fastening connector body 40 also comprises the connector portion 44 as shown in FIGS. 1 to 4 having an axial passage 62 capable of being used for either delivery of fluid into the cutting tool or storing tissue or bone waste removed during the cutting operation.

Figure 17:
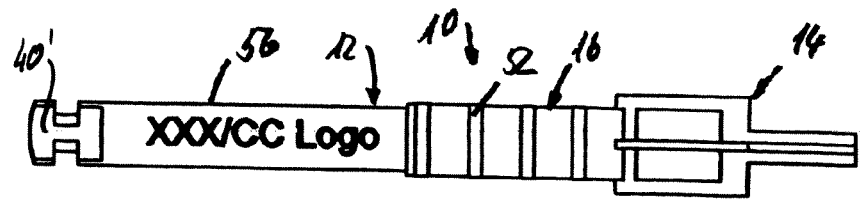
FIG. 17 is a plane view of a sixth cutting tool according to another embodiment, which tool is used for drilling operations.
Figure 18:
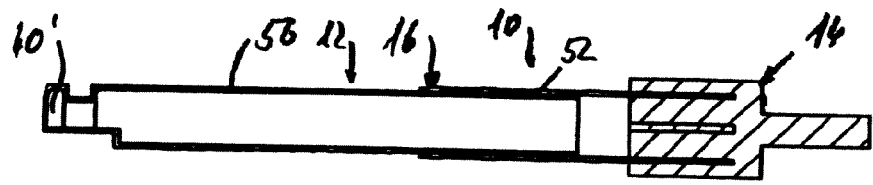
FIG. 18 is a longitudinal sectional view of the sixth cutting tool.
Figure 19:
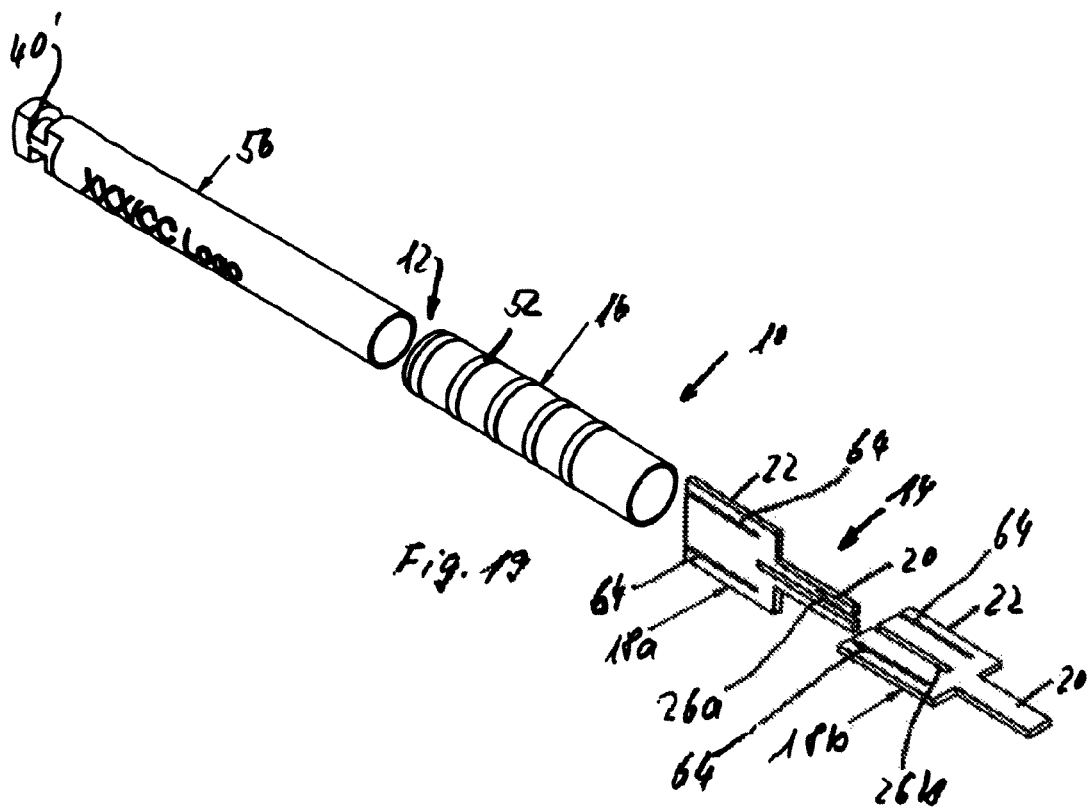
FIG. 19 is an exploded perspective view of the sixth cutting tool.

A sixth embodiment of the cutting tool 10 shown in FIGS. 17 to 19 comprises a further pipe section 56 with an integrally formed fastening connector part 40' of the same design as the pipe section 16 shown in FIGS. 5 to 7. This further pipe section 56 is force fittingly driven into the pipe section 16 of the same design as the pipe section shown in FIGS. 8 to 10 and 14 to 16 with the exception of the absent monitoring window 50.

The tool head consists of two cut-outs 18a, 18b with a rectangular working portion 20 and a rectangular fastening portion 22 with a width greater than the outer diameter of the pipe section 16 and the width of the working portion 20. Consequently slots 26a and 26b of the cut-outs 18a, 18b allow the cross-wise engagement of the cut-outs 18a, 18b as already described in connection with the embodiment shown in FIGS. 1 to 4.

The cut-outs 18a, 18b further comprise lateral slots 64 beginning at the rear end of the fastening portion 22, running in the axial direction of the cutting tool 10 and ending a distance from the front end of the fastening portion 22. When attaching the tool head 14 and the pipe section 16, the wall of the pipe section 16 is inserted into these lateral slots 64.

Also these cut-outs 18a, 18b are manufactured by punching a drawn metal sheet.

A seventh embodiment of the cutting tool 10 shown in FIGS. 20 to 22 comprises an identical further pipe section 56 as the cutting tools of FIGS. 8 to 13 and 17 to 19. The further pipe section 16 shown in FIGS. 20 to 24 does not comprise protuberances and a monitoring window; it is simply a section sawn from a drawn pipe.

The tool head 14 consist of two cut-outs 18a, 18b with complementary slots 26a and 26b attached in a cross-wise manner. Furthermore, the cut-outs 18a, 18b comprise lateral slots 64—as described in connection with the FIGS. 17 to 19—for the collet of the wall of the pipe section 16. In contrast to the embodiment of FIGS. 17 to 19, the cut-outs 18a, 18b of the present embodiment comprise a fastening portion 20, the inner part of which—arranged in the duct 38 of the pipe section—is longer than the outer part.

FIGS. 23 to 25 show an eighth embodiment of the cutting tool 10 with a further pipe section 56 as already known from the FIGS. 8 to 13 and 17 to 22. In contrast to the embodiments shown in said Figures, the pipe section 16 of the present embodiment is driven into the further pipe section 56; the diameter of the pipe section 16 is smaller than the diameter of the further pipe section 56. The pipe section 16 comprises circumferential protuberances 52 and a monitoring window 50 as already described.

The two cut-outs 18a, 18b of the tool head 14 have the form of a brick and comprise complementary slots 26a, 26b to make the cross-wise arrangement possible as well as lateral slots 64 for the wall of the pipe section 16. In contrast to the previously described embodiments where the slots 26a and 26b are of the same length, in the present embodiment the length of the slot 26a is shorter than the length of the slot 26b. The lateral slots 64 go from the rear end of the cut-outs 18a, 18b close to the front edge 24 so that in the assembled state the pipe section 16 ends only a small distance from the front edges 24.

It is further noted that at least one of the protuberances 52 is arranged in the lateral slots 64 to give by means of a force fitting stability to the small tongue-like parts of the cut-outs 18a, 18b arranged radially outside of the pipe section 16.

A ninth embodiment of the cutting tool 10 shown in the FIGS. 26 to 29 comprises a pipe section 16 with protuberances 52 and a monitoring window 50 similar to that disclosed in FIGS. 8 to 10 and 14 to 16. But, the radial inner edge 66 on the front end side of the pipe section 16 is beveled.

The cut-outs 18a and 18b comprise complementary slots 26a, 26b for the cross-wise arrangement of the cut-outs 18a, 18*b* to the tool head 14. The protruding working portions 20 of the cut-outs 18*a*, 18*b* have the form of an isosceles triangle with cut basis corners. Seen in the radial direction, the working portions 20 project from the pipe section 16 only for a very small amount.

As best shown in FIG. 28, the width of the fastening portions 22 in the rear half is smaller than in the front half joining the working portions 20. Consequently, a force fitting between the cut-outs 18*a*, 18*b* and the pipe section 16 occurs only in the front half of the fastening portions 22. The introduction of the fastening portions into the pipe section 16 is thereby simplified.

The further pipe section 56 comprises in the front end region a contraction 68 created for example by stamping or swaging. Also this contraction 68 simplifies the introduction of the further pipe section 56 into the pipe section 16, since the contraction 68 does not build a force fitting with the pipe section 16. The force fitting is built in a region following the contraction 68.

A fastening connector body 40, without a passage 62, is driven into the rear end region of the further pipe section 56.

Figure 30:
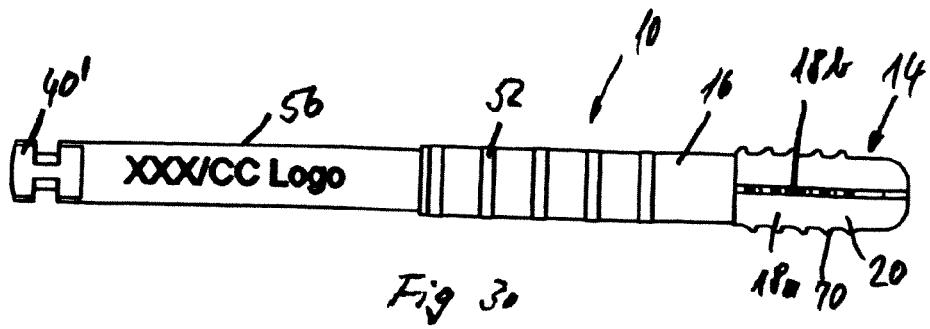
FIG. 30 is a plane view of a tenth cutting tool according to another embodiment, this tool being a tapping tool for making a screw thread.
Figure 31:
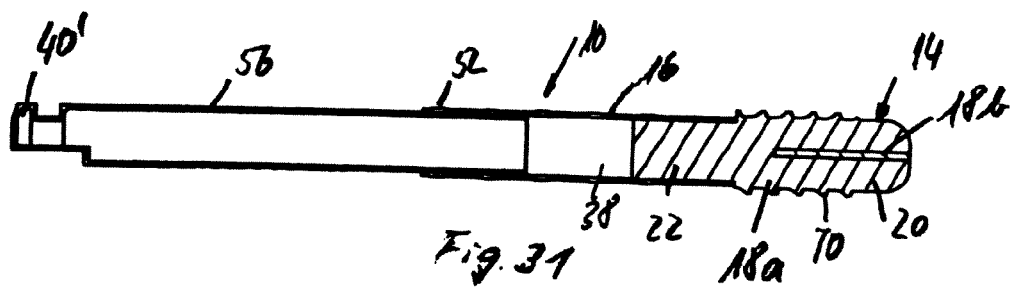
FIG. 31 is a longitudinal sectional view of the tenth cutting tool.
Figure 32:
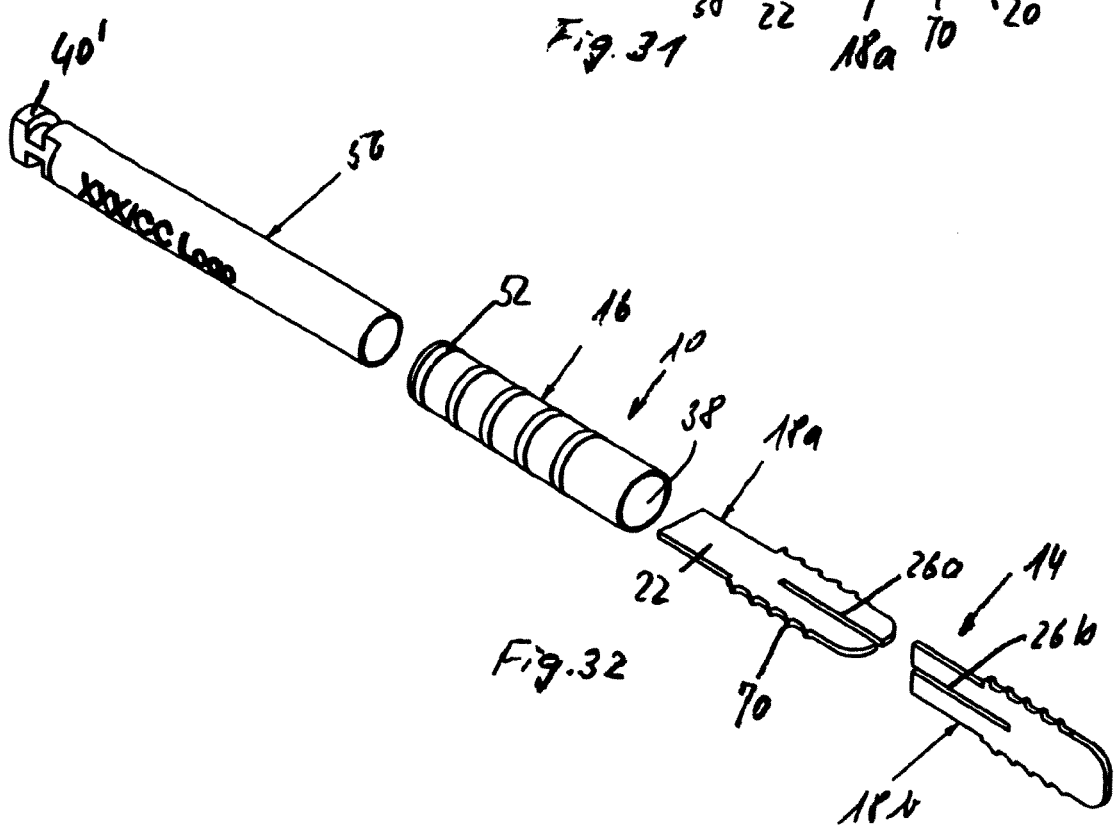
FIG. 32 is an exploded perspective view of the tenth cutting tool.

The pipe section 16 and the further pipe section 56 of a tenth embodiment of the cutting tool 10, shown in the FIGS. 30 to 32, are of the same design as those of the embodiment shown in FIGS. 17 to 19.

As already described in connection with other embodiments also the two cut-outs 18*a* and 18*b* of the present embodiment comprise complementary slots 26*a*, 26*b*. The approximately rectangular working portion 20 with chamfered front corners comprises radially protruding teeth 70 offset in the axial direction, in order to make it possible to form a screw thread in the bone. In the assembled state the rectangular fastening portions 22 of the cut-outs 18*a* 18*b* are located completely in the duct 38 of the pipe section 16.

For most applications, it will be sufficient to have two inserted blades in the form of cut-outs 18*a*, 18*b*. It is possible, however, to produce cutting tools 10 with three or four inserted cut-outs 18*a*, 18*b*, 18*c*, 18*d* such as the embodiment shown in the FIGS. 33 to 35. This cutting tool 10 may be used for machining spherical cups, for example in a bone, or for forming a chamfer at the entrance of a drilled hole. For that purpose the working portion 20 of the cut-out 18*a*, 18*b*, 18*c*, 18*d* is circular. A rectangular fastening portion 22 joins the working portion 22 whereby the fastening portions 22 of the cut-outs 18*a*, 18*b* and 18*c* are of the same axial length whereas the cut-out 18*c* is smaller.

The cut-out 18*a* comprises only one central slot 26*a* beginning at the front end of the cut-out 18*a*. The slot 26*a* is in the first three-fourths of its length wider than in the last fourth. The cut-out 18*b* has two slots, a slot 26*a* beginning at the front end of the cut-out 18*b*, equally wide as the wider part of the slot 26*a* in the cut-out 18*a*, and a slot 26*b* beginning at the rear end and equally wide as the smaller part of the slot 26*a* of the cut-out 18*a*. The cut-out 18*c* also comprises two slots, a small slot beginning at the front end and a wide slot beginning at the rear end. The rear slot ends—in the assembled state of the tool head 14—by the closed end of slot 26*a* of the cut-out 18*b*. The cut-out 18*d* has only one small slot 26*b* beginning at the rear end of this cut-out. The widths of the slots 26*a* and 26*b* are chosen such that the cut-outs 18*a* and 18*b* can be assembled in a 90° position relative to each other and such that the cut-outs 18*c* and 18*d* can be assembled in a 90° position as well as with an offset of 45° in respect of the cut-outs 18*a* and 18*b*.

The assembled tool head 14 is then driven, with the rear end of the fastening portion 22 in front, into the pipe section 16, having the same design as that shown in FIGS. 30 to 32. The pipe section 16 is connected to the further pipe section 56 as already known from previous examples.

The fastening connector portion 40' of all respective embodiments may have an axial passage for the supply of fluid into the duct 38 and to the tool head 14. The metal parts of all embodiments are preferably made from steel of medical quality.

In all disclosed embodiments, the parts of the cutting tools 10 are connected by force fit. The parts may be likewise be fastened by welding, for example by ultrasonic welding, bonding or form fit. Thus, it is possible to locally deform assembled parts, for example by applying a radially inwardly directed force in order to strengthen the force fit or to create a form fit.

The different embodiments of the cutting tools 10 according to the present invention are based on a modular construction system that allows the manufacture of a variety of different cutting tools 10 by using a relative small number of different parts.

The invention claimed is:

1. A disposable rotary cutting tool for dental applications comprising:
    a tubular tool shank comprising a drawn metal pipe section having a uniform diameter over its entire length;
    a tool head comprising a drawn metal tube section having a uniform diameter over its entire length, wherein the tool head has a first open end and a second open end, the first open end of the tool head has a crown of saw teeth forming a circumferential cutting surface, the crown of saw teeth having the same diameter as the rest of the tool head; wherein the second open end of the tool head, opposite the first open end, comprises a bushing, wherein the tool shank is inserted into the bushing, wherein the tool head is force fit connected to the tool shank; and
    a fastening connector that is connected to the tubular tool shank.

2. Cutting tool according to claim 1, wherein the tool head is manufactured by non-cutting machining.

3. Cutting tool according to claim 2, wherein the fastening connector is formed by deformation of the metal pipe section, in an end region away from the tool head.

4. Cutting tool according to claim 1, wherein the metal tube section includes a cut-out or stamped radial monitoring window.

* * * * *